United States Patent [19]

Rozencwaig

[11] Patent Number: 4,771,056

[45] Date of Patent: Sep. 13, 1988

[54] METHOD OF MEDICAL TREATMENT WITH SEROTONIN ANTAGONISTS

[76] Inventor: Roman Rozencwaig, 1440 St. Catherine St., West Suite 814 RR, Montreal, Québec, Canada, H3G 1R8

[21] Appl. No.: 15,109

[22] Filed: Feb. 13, 1987

Related U.S. Application Data

[63] Continuation-in-part of Ser. No. 770,440, Aug. 29, 1985, Pat. No. 4,661,500.

[51] Int. Cl.⁴ ............................................ A61K 31/445
[52] U.S. Cl. .................................................... 514/325
[58] Field of Search ......................................... 514/325

[56] References Cited

U.S. PATENT DOCUMENTS 4,444,778 4/1984 Coughlin .............................. 514/324

OTHER PUBLICATIONS

Chemical Abstracts 97:409t (1982).
Chemical Abstracts 100: 203268z (1984).

*Primary Examiner*—Jerome D. Goldberg
*Attorney, Agent, or Firm*—Foley & Lardner, Schwartz, Jeffery, Schwaab, Mack, Blumenthal & Evans

[57] ABSTRACT

Treatment of patients suffering from cancer, acquired immuno deficiency syndrome, multiple sclerosis, by administration of a serotonin antagonist, the administration taking place once a day during the evening, preferably after sunset.

9 Claims, No Drawings

METHOD OF MEDICAL TREATMENT WITH SEROTONIN ANTAGONISTS

CROSS-REFERENCE TO RELATED APPLICATION

This application is a continuation-in-part of copending application Ser. No. 770,440 filed Aug. 29, 1985, now U.S. Pat. No. 4,661,500.

BACKGROUND OF INVENTION (a) Field of the Invention

This invention relates to a method of treatment of conditions such as bladder carcinoma, lung carcinoma, breast carcinoma, carcinoma of adrenal cortex, or pancreatic carcinoma by serotonin antagonists and primarily cyproheptadine.

(b) Description of Prior Art

There is a considerable number of studies on the ageing process, including the factors and agents responsible, and there are some suggestions to alleviate it. Some of the diseases often associated with old age include cancer, various heart diseases, arthritis, etc. In two articles which have appeared in 1982—P. S. Timiras et al, The Ageing Brain: Cellular and Molecular Mechanisms of Ageing in the Nervous system, edited by E. Giacobini et al, Raven Press, New York—Developing and Ageing Brain Serotonin Systems; and P. S .T. Timiras et al, Age and Aging (1982) 11, 73-88—there are discussions on the effect of serotonin on the ageing process. These studies have shown that serotonin accumulates in the central nervous system, with increasing age in a linear fashion, whereas its metabolite, melatonin, produced in the pineal gland decreases during aging.

The chemical cyproheptadine is a known serotonin antagonist and although other serotonin antagonists are known, the present discussion will be restricted to cyproheptadine because it is most available at present with least side effects, although the present invention is not restricted to applications of cyproheptadine. Numerous references describe the various medical uses of cyproheptadine. The following list is only partial:

(1) Studies of Mechanism of Cyproheptadine-induced Weight Gain in Human Subjects, John N. Stiel et al, Metabolism, March, 1970, 19(3) pp?.

(2) Experimental Study on Atherosclerosis, an Attempt at its Prevention and Treatment, Acta Pathol. Jap. February 1969, 19(1) pp. 15-43.

(3) A preliminary Report on BC-105: a new Antidepressant, Psychosomatics, January-February 1969, 10(1) pp. 51-2.

(4) More on Cyproheptadine in Cushing's Disease, New England J. Med. Mar. 10, 1977, 296(10) pp. 576-7.

It is worthwhile considering the potential therapeutic use of cyproheptadine against cancer because this disease continues to be a major cause of death in western society despite the massive research efforts. Cyproheptadine has been investigated in cancer not as a specific therapeutic agent against the growth and spread of the cancer cells but as a way of overcoming the anorexic effects of the disease by stimulating appetite.

The ageing process is characterized by a group of progressive diseases such as arteriosclerotic heart disease, cardiovascular accidents, hypertension, arthritis, diabetes; and an increase in age-related cancers. The serotonergic neurotransmitter system which is dominant in the central nervous system, and which directly effects the entire neuroendocrine system via the hypothalamic pituitary axis, is proposed in the prior art to be responsible for the ageing process for the following reasons.

By referring to the tables in the references of the Timiras et al mentioned above, it can be seen that serotonin promotes cystogenesis and causes general chronic inflammatory fibrotic changes, gradually leading to a replacement of normal tissues by chronic inflammatory debris-forming soars which in turn lead to increases in rigidity, decreased transport of nutrients and subsequent organ failure.

It is therefore believed that by administering an agent which is a serotonin-antagonist and which can cross the blood brain barrier to act within the central nervous system, this serotonin-antagonist would then act in effect as an anti-ageing substance and in that respect may also be used in the treatment of diseases of the aged, and other acute diseases.

SUMMARY OF THE INVENTION

It is an object of the present invention to provide a method of treatment of conditions such as bladder carcinoma, lung carcinoma, breast carcinoma, carcinoma of adrenal cortex, or pancreatic carcinoma by administering a serotonin antagonist in such a way to alleviate such diseases.

It is another object of the present invention to provide a method for the treatment of patients suffering from bladder carcinoma, lung carcinoma, breast carcinoma, carcinoma of adrenal cortex, or pancreatic carcinoma which comprises administering a serotonin antagonist to the patients, this administration essentially taking place once a day every evening, preferably after sunset.

In accordance with a preferred embodiment of the invention, the administration takes place between about 6 and about 10 o'clock p.m., and preferably as soon as possible after sunset.

In accordance with another preferred embodiment of the invention, the administration takes place with doses of about 0.5 to 4 mg. of serotonin antagonist.

Preferably, the serotonin antagonist is conditioned in a suspension or in a tablet. The preferred serotonin antagonist obviously comprises cyproheptadine, because it is readily available as an over the counter drug.

RESULT OF TEST TREATMENTS

The method of treatment according to the invention consists of the administration of cyproheptadine in a dose from 0.5 to 4 mg. orally either by a tablet or in liquid suspension. The administration took place every evening between 6 to 10 p.m., depending on the season, earlier in winter and later in the summer, bearing in mind that it should normally take place as soon as possible after sunset. This invention will now be illustrated by means of the following test cases which illustrate positive results obtained in treatment of bladder carcinoma, lung carcinoma, breast carcinoma, carcinoma of adrenal cortex, or pancreatic carcinoma.

TEST NO. 1

Patient A suffering from cancer of the bladder.

This patient had a bladder carcinoma and was treated as indicated above for a period of weeks. This patient has recovered without having any recurrence of the disease and is presently maintained at a maintenance dose of cyproheptadine 4 mg. every evening.

TEST NO. 2

Patient B having bladder carcinoma.

This patient was treated in a similar manner as patient A and has also recovered from the disease while being maintained at a maintenance dose of cyproheptadine 4 mg. every evening.

TEST NO. 3

Patient C having lung cancer.

This patient had inoperable lung carcinoma which was irradiated concurrently with cyproheptadine treatment as mentioned above. Ten percent of patients with lung carcinoma receiving radiation therapy survive one year. Patient C was treated in a manner indicated above and is now free of cancer recurrence 18 months after the initiation of cyproheptadine treatment, which the patient continues to take every evening.

TEST NO. 4

Patient D having breast cancer.

Patient, a 56 year old female with a breast carcinoma, was operated for a radical masectomy and is maintained on a dose of 2 mg. of cyproheptadine every evening. After undergoing the above treatment, she is presently free of disease two years after surgery.

TEST No. 5

Patient E, having breast cancer.

M.B., a 72-year old lady, was found a year ago with a tumor of the right breast. It was about 9 cm in diameter and ulcerating. She did not seek medical help prior to that time. She was referred to a surgeon at the hospital but refused surgery. The only treatment she received was local irradiation and 4 mg periactin gHS, in the manner indicated above.

As of the present time her tumor has completely regressed leaving a small dimple at the site of the tumor. She has regained most of her weight loss and feels well. She continues taking periactin as above. According to the radiotherapist treating her, "It is very unusual to have such a great reduction in this type of tumor by radiation alone."

It is believed that periactin contributed significantly to this patient's recovery from cancer, as well as to her increased appetite and sense of well-being.

TEST NO. 6

Patient F having cancer of the adrenal cortex.

M.J. is a 20 year old female with a one year history of carcinoma of the adrenal cortex before undertaking periactin treatment. By that time her tumor had spread rapidly to involve her lungs, pleura, liver as well as other tissues in the abdomen, and obstructing the inferior vena cava. She has received various protocols of chemotherapy without apparent benefit. Her appetite remained poor, she continued to lose weight, was unable to walk and was quite depressed. In short, she continued to deteriorate rapidly.

In May 1986 she was started on periactin once a day in the evenings. Within one week there was considerable improvement. Her appetite returned to normal, her depression disappeared, she became physically more active and was doing well. During subsequent months she received two courses of chemotherapy. Of all the persons she knew who were on that program, she was the only one without side effects and it is believed that this is attributable to pericatin.

A recent C.A.T. scan revealed that she still has tumor in her lungs and liver. Nevertheless, the patient is eating well and felling well, putting on weight and carries on with her daily activities. Presently, her condition is stable.

In this case, periactin appeared to bring about a definite increase in a feeling of well being and a decrease in suffering due to the disease itself and to other chemotherapeutic procedure she had been receiving.

TEST NO. 7

Patient G having cancer of the pancreas.

A.Z. a 52-year old female, presented herself at the hospital and was diagnosed as having a pancreatic carcinoma with diffuse spread. The tumor board at the hospital felt that her disease was so widespread that no further treatment could be given other than periactin.

After one week of treatment with periactin 4 mg qHS in the manner indicated above, the patient claimed that her pain had subsided and she was able to start eating again. After another week and further improvement, she was discharged from the hospital.

She did well at home for about three months. However, at the end of that time she was readmitted to hospital and died 2 days later of pneumonia.

In this case, the periactin apparently decreased the patient's pain and depression and improved her appetite. This case illustrates the value of periactin in late stage cancer.

As mentioned above it was suspected that a serotonin antagonist would be useful in the treatment of the diseases of the aged. However, the prior art is mute with regard to the successful treatment of bladder carcinoma, lung carcinoma, breast carcimona, carcinoma of adrenal cortex, or pancreatic carcinoma. It is believed that the treatment according to the invention is successful in view of the following.

It is suggested that cyproheptadine acts not merely as a serotonin antagonist but at the same time it is a melatonin agonist. We propose that it is the relative increase of serotonin over melatonin as well as the absolute decrease of melatonin that is of significance at least to the posology indicated above. Thus, it is suggested that cyproheptadine acts as a serotonin antagonist and as well as a melatonin agonist. In this respect, this is the reason why it has to be given in the evening, especially as soon as possible after sunset, since this is when the action of melatonin takes place. This action of cyproheptadine when administered in the evening is new and has not previously been described, at least to my knowledge. In other words, the dual function of melatonin agonist and serotonin antagonist of cyproheptadine has not been shown in the prior art.

The prior art has shown that when given during the day, the serotonin antagonist may actually be harmful. However, in view of the dual properties of the serotonin antagonist, when administered at night, the effect is beneficial.

Of course, it is within the scope of the present invention to use other serotonin antagonists in addition to cyproheptadine. This disclosure was restricted to that particular compound because it was more readily available.

I claim:

1. A method for the treatment of patients. suffering from bladder carcinoma, lung carcinoma, breast carcinoma, carcinoma of adrenal cortex, or pancreatic carcinoma which comprises orally administering to said patients doses of about 0.5 to about 4 milligrams of a serotonin antagonist consisting of cyproheptadine, said administration taking place once a day every evening.

2. A method according to claim 1, wherein said administration takes place between about 6 and about 10 o'clock p.m.

3. A method according to claim 1, for the treatment of bladder carcinoma.

4. A method according to claim 1, for the treatment of lung carcinoma.

5. A method according to claim 1, for the treatment of breast carcinoma.

6. A method according to claim 1, for the treatment of carcinoma of adrenal cortex.

7. A method according to claim 1, for the treatment of pancreatic carcinoma.

8. A method according to claim 1, wherein said cyproheptadine is conditioned in a suspension.

9. A method according to claim 1, wherein said cyproheptadine is conditioned in a tablet.

* * * * *